Figure 1:
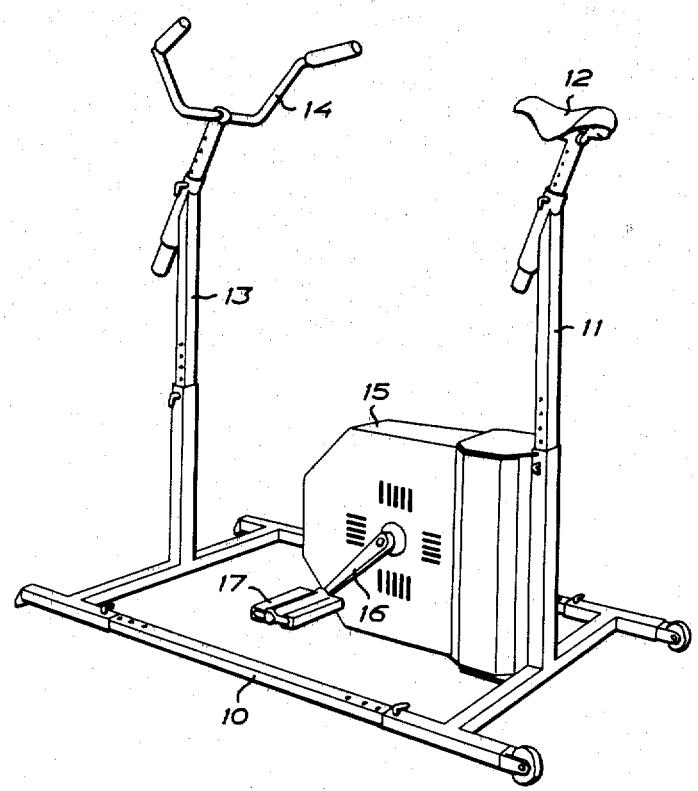

United States Patent [19]
Forsman

[11] 4,084,810
[45] Apr. 18, 1978

[54] ENERGY ABSORBING UNIT FOR PHYSICAL EXERCISING DEVICES

[76] Inventor: Lars Östen Forsman, Lindogatan 1, S-253 72 Helsingborg, Sweden

[21] Appl. No.: 491,975

[22] Filed: Jul. 26, 1974

[30] Foreign Application Priority Data

Aug. 2, 1973 Sweden ................................ 7310639

[51] Int. Cl.² ...................... A63B 69/16; A63B 21/24
[52] U.S. Cl. .......................................... 272/73; 74/686; 128/25 R; 272/129; 272/DIG. 6; 310/75 B
[58] Field of Search ........................ 272/73, 116, 129; 128/25 R, 25 B; 35/29 R; 310/93, 67 A, 75 B, 75 C, 166, 198; 74/686, 793

[56] References Cited

U.S. PATENT DOCUMENTS

| | | | |
|---|---|---|---|
| 1,515,321 | 11/1924 | Ahlm et al. | 74/686 |
| 1,862,471 | 6/1932 | Farrell | 74/686 |
| 1,893,346 | 1/1933 | Winther et al. | 74/686 X |
| 2,436,936 | 3/1948 | Page | 74/686 X |
| 2,622,217 | 12/1952 | Anderson, Jr. | 310/166 |
| 2,784,591 | 3/1957 | Shoor | 272/73 X |
| 3,067,631 | 12/1962 | Hayasaka et al. | 74/686 |
| 3,395,698 | 8/1968 | Morehouse | 272/73 UX |
| 3,400,793 | 9/1968 | Norris et al. | 272/129 X |
| 3,408,517 | 10/1968 | Willyoung | 310/198 |
| 3,468,193 | 9/1969 | O'Mahony | 74/686 |
| 3,505,992 | 4/1970 | Jaeger | 272/73 R X |
| 3,624,435 | 11/1971 | Bunner | 310/93 |
| 3,624,436 | 11/1971 | Jaeschke | 310/93 |
| 3,624,438 | 11/1971 | Hoyler | 310/93 |
| 3,744,480 | 7/1973 | Gause et al. | 272/73 X |
| 3,765,245 | 10/1973 | Hampl | 272/73 UX |
| 3,767,195 | 10/1973 | Dimick | 272/73 |
| 3,802,698 | 4/1974 | Burian et al. | 272/73 |
| 3,824,993 | 7/1974 | Grant | 128/25 R |
| 3,845,756 | 11/1974 | Olsson | 272/73 |
| 3,869,121 | 3/1975 | Flavell | 272/129 |

FOREIGN PATENT DOCUMENTS

| | | | |
|---|---|---|---|
| 1,002,341 | 10/1951 | France | 74/686 |
| 1,557,137 | 1/1969 | France | 128/25 R |
| 2,019,887 | 11/1971 | Germany | 310/68 C |
| 1,135,764 | 12/1968 | United Kingdom | 310/67 A |

*Primary Examiner*—Richard C. Pinkham
*Assistant Examiner*—Arnold W. Kramer

[57] ABSTRACT

An energy absorbing unit for physical exercising devices is arranged as an asynchronous motor the stator of which has windings to be connected to an AC supply and cooperates with the rotor of ferromagnetic material having a circular circumference, and an input shaft and an epicyclic gearing arranged inside the rotor circumference operatively connecting the input shaft to the rotor with the input shaft adapted to be driven by the training person, in order to generate an electromagnetic motive force on the rotor to tend to drive it in the direction opposing movement of the shaft by the training person and thereby act as a braking force on the shaft independently of the movement thereof.

9 Claims, 7 Drawing Figures

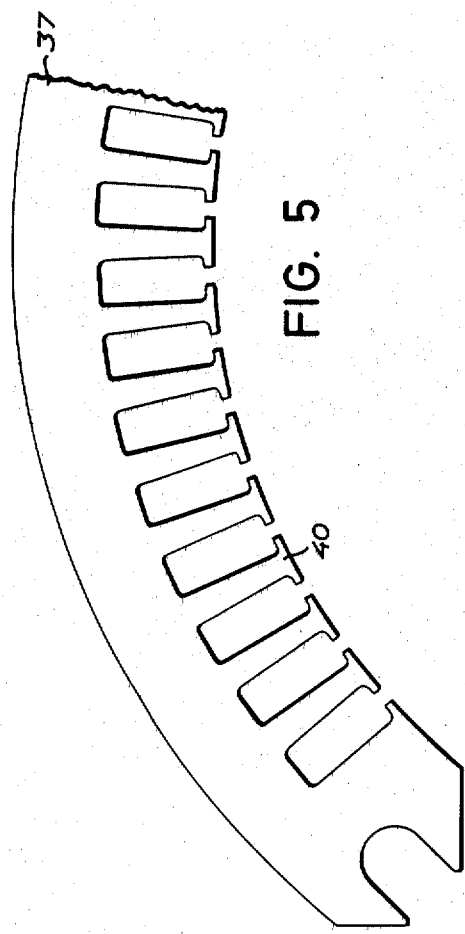
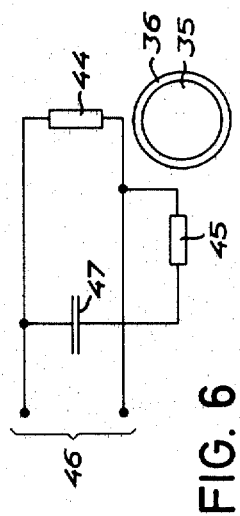
FIG. 5
FIG. 6

ENERGY ABSORBING UNIT FOR PHYSICAL EXERCISING DEVICES

The present invention relates to an energy absorbing unit for physical exercising devices of different types comprising a frame having a member movably journalled therein, which is adapted to be driven by the training person by means of the power transmission system of the exercising device, and further comprising a brake for restraining the movement of said member by an electromagnetic braking action, provided by an asynchronous motor.

In prior art energy absorbing units of this type the unit is constructed as an eddy current brake or as a generator the output power of which is transformed to heat in a resistor connected to the generator circuit. In that case the braking force is dependent upon the rotational speed, and in order to control the braking force and to keep it at a constant value independent of the rotational speed complicated devices have to be combined with the energy absorbing unit. Moreover, the unit exerts no braking force when it is inoperative; until the movable member of the unit is being driven no braking force will be generated, and as a rule the movement also has to attain a predetermined speed for the braking force to be effective.

The principal object of the invention is to provide an energy absorbing unit of the kind referred to above which, without being of a complicated structure, provides an exactly determinable braking force and allows the work which shall be produced by the training person to be accurately observed and controlled by means of relatively simple apparatus so that the performance can be matched to the physical condition and strength of the training person.

This object is achieved according to the invention by providing an energy absorbing unit for physical exercising devices of the kind referred to above wherein the unit is arranged as an asynchronous motor comprising a wire-wound stator operatively cooperating with said movable member, which can be connected to a single or three phase AC supply and generates an electromagnetic braking force on the movable member independently of the movement thereof, and in a direction of rotation opposite to the direction of rotation imposed on the movable member when operated by the training person.

Figure 2:
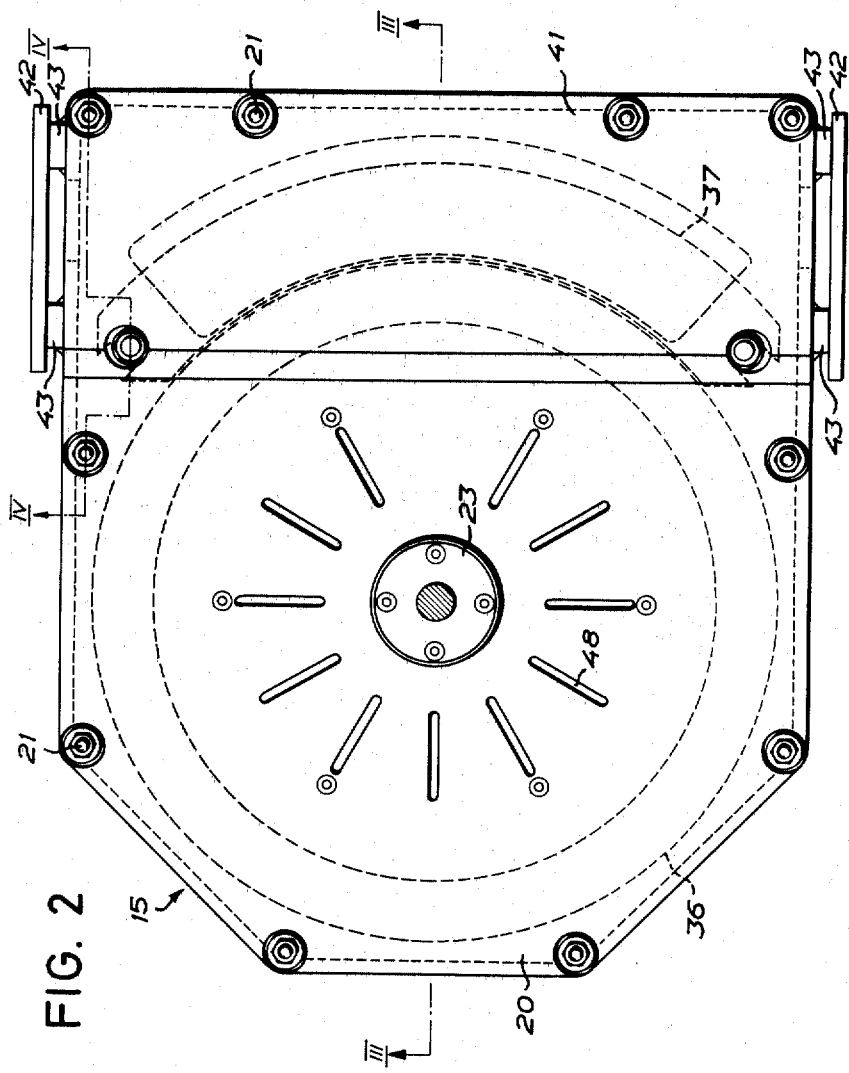
Figure 3:
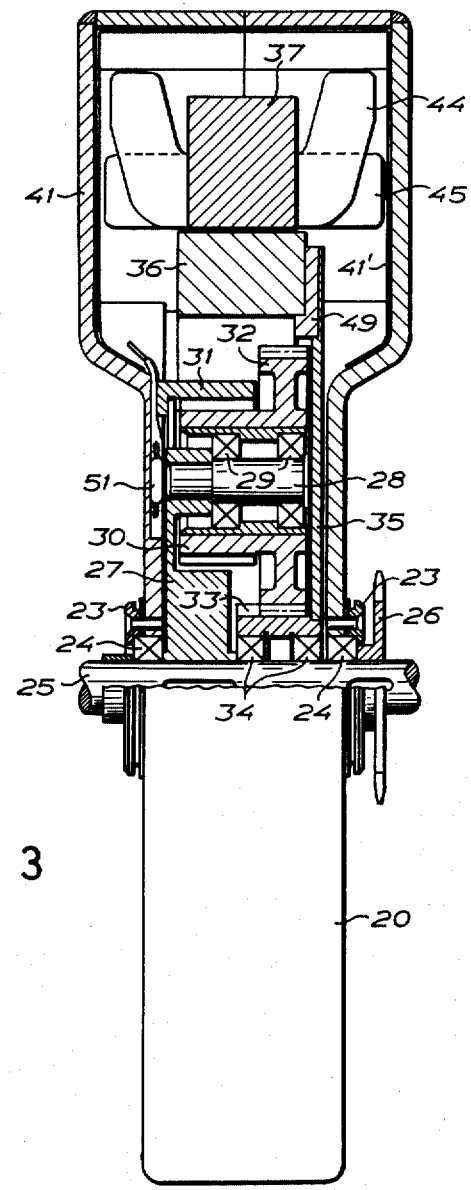
Figure 4:
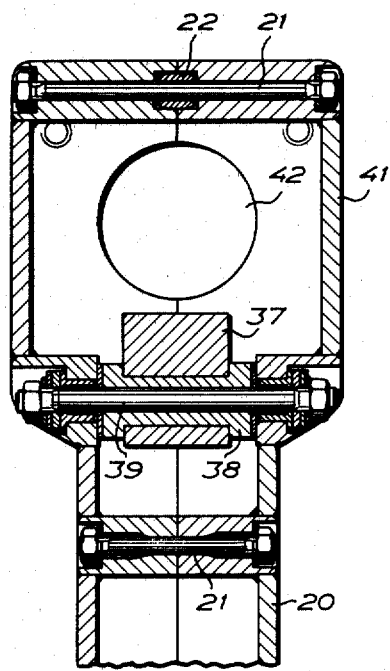
Figure 7:
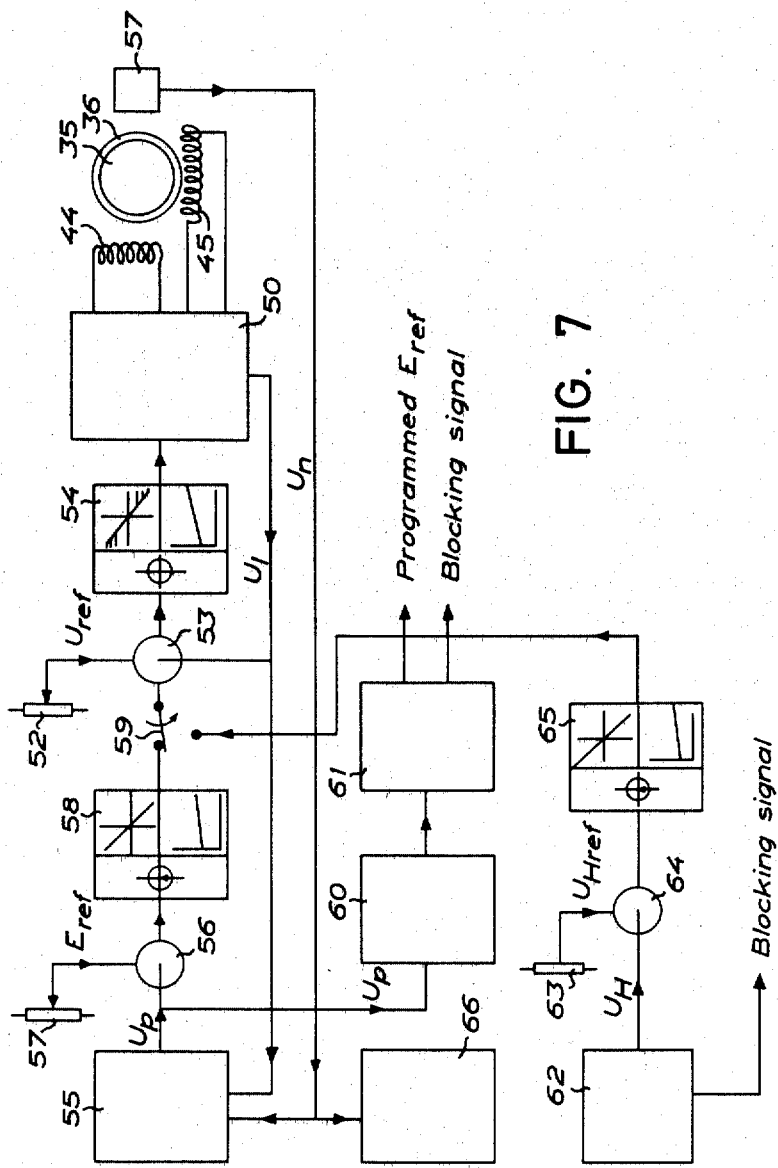

In order to illustrate the invention an embodiment thereof will be described in more detail below reference being made to the accompanying drawings in which FIG. 1 is a perspective view of an exercising device of the bicycle type (bicycle ergometer) provided with the energy absorbing unit according to the invention, FIG. 2 is an enlarged side view of the energy absorbing unit, FIG. 3 is a further enlarged cross sectional view along the line III — III in FIG. 2, FIG. 4 is a further enlarged cross sectional view along the line IV — IV in FIG. 2, FIG. 5 is a side view of a laminated metal sheet core forming part of the unit, FIG. 6 is an electric circuit diagram of the unit when arranged to be connected to a single phase AC supply, and FIG. 7 is an electric circuit diagram of a control system of the energy absorbing unit according to the invention.

The exercising bicycle (bicycle ergometer) shown in FIG. 1 comprises a rectangular bottom frame 10 of square cross sectional tubes, from which projects a standard 11 which can be adjusted vertically and has a seat 12, and a standard 13 which also can be adjusted vertically and has a support 14 formed as bicycle handle bar. In the present case the bottom frame and the standards are made of tubing having square cross section but obviously the stand formed by these elements may be constructed of tubes or bars of other types and be asssembled in another way. Connected with standard 11 is an energy absorbing unit 15 according to the invention. This unit has a through drive shaft (not seen in FIG. 1) with a crank 16 arranged at each side of the energy absorbing unit these two cranks projecting in diametrically opposite directions, and on each crank there is rotatably journalled a pedal 17.

The exercising device disclosed in FIG. 1 is an illstrative example of a device in which the energy absorbing unit according to the invention may be used. However, this unit may be combined in countless ways with members of different types having a rotating or reciprocating movement, which are adapted to be operated by arms and/or legs and may be coupled to the unit by means of conventional transmissions, comprising reduction gearing or not, or may be connected directly to the drive shaft of the unit as are the treadles in FIG. 1. Particularly it should be mentioned that the members which are operated manually for driving the energy absorbing unit may comprise members for performing a rowing movement or a picking movement such as occurs during weaving in a conventional loom.

The person who shall exercise or perform other physical training by using the exercising device described is seated on the seat 12 and holds on to the handle bar 14. With the legs he operates the treadles formed by cranks 16 and pedals 17 exactly as during cycling in order to rotate the drive shaft of unit 15. The direction of rotation of the drive shaft corresponds to a progressive forward movement of a cycle. Rotation in this direction is opposed by the asynchronous motor, which when the motor is turned on seeks to rotate the drive shaft in the opposite direction. In this manner, the rotational movement produced by the training person operating the treadles is braked by means of the unit wherein the kinetic energy produced will be converted to heat. This unit shall now be described in detail reference being made to FIGS. 2 to 6.

The energy absorbing unit includes an outer housing 20 of a welded or moulded material comprising two halves which are interconnected by means of stud connections 21 and are exactly fixed in relation to each other by means of a number of guides 22 disposed between the halves of the housing. In the present case this housing forms the frame or stand of the unit but it may also function as an enclosing housing only which possibly forms an integral part of the apparatus wherein the energy absorbing unit is included as an operative part thereof, a separate frame then being disposed inside the housing, which comprises, for instance, a pair of interconnected bearing plates according to the same system which is usual in clock movements. However, in the present case the housing is arranged as a frame, and centrally in the housing there are mounted by means of bearing cape 23 roller or ball bearings 24 for journalling the drive shaft mentioned above, which is here designated 25, cranks 16 being mounted thereon. However, the cranks are not shown in FIGS. 2 to 4 which disclose, as a possible modification, a sprocket 26 keyed to the shaft, which may in turn be operatively connected to cranks of one type or other by means of a chain transmission.

Inside the housing there is keyed to the shaft a planet wheel carrier 27 having a stub shaft 28 on which there is journalled by means of ball bearings a planet wheel 30. Several stub shafts 28 and associated wheels 30 may be arranged although in this case a single one only is shown. Inside the housing there is also provided a stationary gear 31 which comprises a ring having gear teeth on the inner side thereof and which may be mounted inside the housing or may form an integral part thereof the planet gear engaging this gear ring. The planet wheel is formed integrally with a larger gear wheel 32 which is thus rotated together with the planet wheel on the stub shaft thereof, and said gear wheel in turn engages a sun wheel 33 which is rotatably journalled on shaft 25 by means of roller or ball bearings. However, the epicyclic gearing thus formed may be provided with a single planet wheel, which means that the planet wheel meshes directly with sun wheel 33 gear wheel 32 being dispensed with. The sun wheel is fixed to or may also form an integral part of a rotor which includes a rotor disc 35 and a rotor rim 36. This rotor accordingly can be driven from shaft 25 the rotational speed thereof being stepped up over the epicyclic gearing described, which is of a compact form and requires a small space.

Rotor rim 36 consists of a ferro magnetic material preferably iron in order to have a low magnetic reluctance and, occasionally, a large mass so that it may operate as a fly wheel in the energy absorbing unit, and on the periphery surface thereof it may have a layer, about 0.5 mm thick, e.g. of copper or another material having a good electrical conductivity. This layer is not, however, necessary for the intended function of the energy absorbing unit.

Rotor 33, 35, 36 forms a short-circuited rotor in an asynchronous motor which includes also a laminated stator 37. In the present case this stator extends outside the rotor rim 36 over part of the circumference of the rotor only as will be clearly seen in FIG. 2, and it is connected at the ends thereof to the housing by means of electrically insulating bushings 38 and stud connections 39, FIG. 4. The stator is formed with pole members 40 which project towards the rotor rim and forms together with the outer periphery surface thereof a small air gap of the order which is common in asynchronous motors. Housing 20 forms a portion 41 which provides a straight passage, open at both ends, through the housing, which has substantially rectangular cross sectional form, FIG. 4, and in this passage the stator is disposed. On the housing are mounted plates 42 which cover the end openings of the passage but are spaced therefrom due to the fact that they are fixed by screws to studs 43 on the housing. These studs thus form spacers in order to provide between the plates and the housing slots through which the passage and accordingly the housing as a whole communicates with the surrounding air. In this manner the passage forms an air duct open at both ends thereof through the housing. Plates 42 may be constructed for mounting the energy absorbing unit to the exercising device and in that case the plates may be formed integrally with the stand of the exercising device. Then, the mounting of the energy absorbing unit on the exercising device is made by connecting the plates by screws to their studs.

On pole members 40 there are arranged windings of double-varnished copper wire alternate pole members each having a coil 44 and 45, respectively. These coils are received by the coil grooves formed in the stator between the pole members thereof, which are preferably provided with electrical insulation, and form part of the electrical circuitry shown in FIG. 6. In this circuit diagram coils 44 and 45 are represented collectively as blocks having corresponding reference numerals. The coils 44 form a main phase in the asynchronous motor and this main phase is connected directly to terminals 46 for connecting the asynchronous motor to a single phase AC supply, the coils 45 being connected to these terminals in series connection with a condensor 47. These coils form the auxiliary phase of the asynchronous motor and thus the asynchronous motor is in this case of the condensor type. However, it is obvious that the asynchronous motor may be of another type, known per se, and may be arranged for connection to a three phase AC supply.

Normally, an asynchronous motor has a certain degree of slip, rotor and magnet flow having the same sense of rotation and the moment characteristic of the motor being dependent upon the rotor resistance. If the direction of the magnet flow is such that it tends to drive the rotor in the opposition direction to the rotational direction imposed on the drive shaft of the unit 15 when the treadles are being operated by a training person there will be provided on the rotor a braking moment which is proportional to the stator currents. Accordingly, this principle for obtaining a braking moment is utilised in the energy absorbing unit according to the invention by connecting the phase windings of the asynchronous motor to the AC supply in such a manner that there will be developed in the rotor a torque which is directed in the opposite direction to that in which the rotor is to be driven by rotating shaft 25, in the present case by treadling pedals 17. The treadling thus will take place against a predetermined resistance defined by the asynchronous motor, which exists when the motor is turned on and will be substantially constant independently of the rotational speed as long as the stator currents are constant. In the circuit according to FIG. 6 means may be easily incorporated for controlling the resistance provided by the asynchronous motor, and for indicating the power supplied to the treadles of the energy absorbing unit as will be described later. Moreover, by a simple modification of the connection of the stator phases of the asynchronous motor it is possible to have the asynchronous motor operate in the intended rotational direction of shaft 25 which may be desirable in certain types of exercise, so called passive exercise, e.g. when persons having reduced strength are being treated. While a training person is operating the treadles, and thereby driving the shaft 25 in a rotational direction opposite to that sought to be imposed by the asynchronous motor, when the motor is turned on, the energy supplied mechanically by the training person will be braked by the motor and will be transformed to heat in the rotor and, for the major part in the stator. However, the stator is dimensioned in such a way that the temperature does ot increase over a permitted value during normal operation. Moreover, there is provided for a good ventilation in the housing for dissipating the heat by the fact that the stator of the asynchronous motor is disposed in said passage 41 in the housing, mentioned above and by the fact that radial ventilation slots 48 are provided in the housing around the centre thereof for air circulation around the rotor. By the rotation of the rotor there will be provided some forced. circulation of air through the housing and this circulation can, of course, be amplified and supported by mounting or forming fan wings or the like on the rotor in a suitable way. However, by the arrangement of passage 41 vertically there will be provided an effective self-circulation of air through this passage thanks to some chimney draft. This disposition of the housing having the passage disposed vertically thus is preferred and is disclosed in FIG. 1 although it is, of course, possible to dispose the housing in other positions when this is found to be suitable considering other conditions in the exercising device.

It should be mentioned that it is not necessary to have the stator arranged outside the rotor. It is also possible to arrange the stator inside the rotor rim or at one side thereof or to construct the stator in such a way that it straddles the rotor rim the form of the rotor of course has to be matched thereto. Also, the stator may be provided with double sets of stator windings.

It will be seen that the stator is electrically insulated from the housing due to the fact that it is supported by the electrically insulating bushings 38. Moreover, part 41 of housing 20 in the area around the stator can have an electric insulation 41′. In order to meet actual electric regulations and still maintain a compact construction it may be suitable to have also the rotor rim 36 electrically insulated from the housing by making the rotor disc 35 at least partically of an electrically insulating material; e.g. part 49 of the rotor may consist of such a material. The gears of the epicyclic gearing in that case suitably are made of a plastics material or the like whereby they are also electrically insulating at the same time as they are of a low friction material.

In an exercising device e.g. a bicycle ergometer of the type disclosed in FIG. 1 it may be required to obtain predetermined functions depending on the type of body training for which it is desired to use the exercising device, and in FIG. 7 there is shown the circuit diagram for an electric control system whereby the most important ones of these functions can be achieved.

One function is to provide a constant braking force in the energy absorbing unit. In order to obtain a constant braking force the current in the stator windings must be controlled in such a way that there will be compensation for current changes due to variations in temperature and rotational speed. For the control of the current in the stator windings and thus the braking force there is provided a current regulator 50 which may comprise a transformer e.g. a rotary transformer (variac) or a semiconductor regulator, having a built in control unit, and for the generation of a signal representing the rpm of the rotor there is operatively connected to the rotor an rpm transmitter 51 of a prior art type. Reference is made also to FIG. 3 where the transmitter is disclosed.

In the control system according to FIG. 7 the control for obtaining a constant braking force is provided by means of a feed-back circuit. On a reference unit 52 (potentiometer) the desired value of the braking force is set as represented by a signal $U_{ref}$ obtained from this unit said signal (reference quantity) being compared in a comparator 53 with a signal $U_I$ supplied by the current regulator 50 and representing the instant currents in the phase windings (variable quantity). The difference signal is supplied to an amplifier 54 having a progressive and integrating system formed by a feed-back circuit. The output signal of this amplifier should be continuously amplitude limited to variable values, which provides a variable maximazation of the braking force, and is supplied to the control unit of the current regulator 50 for keeping the phase currents and thus the braking force constant.

Another desired function is the adjustment of a constant effect. In this case a signal $U_n$ is supplied from the rpm transmitter 51 to a multiplier 55 where this signal will be multiplied by signal $U_I$ also supplied to the multiplier. A signal $U_p = C \cdot U_I \cdot U_n$ will be obtained where C is a scale factor. In a comparator 56 this signal (variable quantity) will be compared with a reference signal $E_{ref}$ (reference quantity) obtained from a reference unit 57 (potentiometer) and the output signal of the comparator will be supplied to an amplifier 58 having a feed-back system of the type P + I the output signal of this amplifier then being supplied to regulator 50 through a switch 59, comparator 53 and amplifier 54 for adjustment of the effect to a constant value. For practical reasons this function has to be limited to a lower limit of rotational speed which is about 35 rpm.

Means may be provided for supplying a warning signal if the maximum braking force will be obtained or the lower rotational speed limit will e underpassed.

If signal $U_p$ is integrated over the time the work performed will be obtained and this is another desired function of the exercising device. This integration may be performed independently of the effect kept constant or not. According to FIG. 7 signal $U_p$ from multiplier 55 for this purpose will be supplied to an integrator 60 and the output signal thereof can be supplied to a programme unit 61 which may be used to portioning the work from time to time when a person is training on the exercising device, e.g. by means of a personal punched card. Moreover, intermittent loading cycles dependent of the work performed (competition feature) may be obtained by means of a programme unit of this type. For this purpose the programme unit supplies a programmed signal $E_{ref}$ and a signal for blocking the current regulator 50.

When heart infarction patients are to be rehabilitated it is desired to have an exact control of the body training and for this purpose there may be provided in the control system a heart pulse unit 62 sensing the pulse of the training person and providing a control in dependence thereof. This is a further desired function of the exercising device. The heart pulse unit can be arranged in such a way that it will provide an alarm signal and a signal for blocking the current regulator 50, if the pulse is too high or too low, if a pulse change occured is relatively too large, if single pulse beats fail and/or the pulse turns too weak, i.e. when the electric signal from the body through the heart pulse unit underpasses a predetermined threshold value. At the occasions when a constant heart pulse is desired during the training a reference signal $U_{Href}$ (reference quantity) from a reference unit 63 (potentiometer) will be compared in a comparator 64 with the signal designated $U_H$ (variable quantity) from the heart pulse unit 62, and the resulting difference signal will be supplied to an amplifier 65 having a feedback system of the type P + I. The time constants should be selected in such a way that no overshooting of the heart pulse will occur, which may be facilitated partly by limiting the braking force. The signal from amplifier 65 will be supplied to current regulator 50 trough switch 59.

The rpm regulator 51 is connected to an rpm indicator 66 which is controlld by signal $U_n$.

Instead of the analog control system described there may be provided a digital control system which has the same functions as the analog system but in many respects will be simpler as far as the construction is concerned since the amplifiers included in the analog system are not provided in the digital system. For the man skilled in the art it would involve no difficulties to make the modification from an analog system to a digital one by guidance of the description of the analog system and, therefore, it would not be necessary to describe here the digital system in more detail.

I claim:

1. An energy absorbing unit for physical exercising devices comprising a frame; a member movably journalled therein comprising a rotor of a ferromagnetic material and having a circular circumference, and an input shaft and an epicyclic gearing arranged inside the rotor circumference operatively connecting the input shaft to the rotor, and having planet wheels, and at least an annular portion of the rotor being made of an electrically insulating material; which member is adapted to be driven by the training person; and said rotor being the rotor of an asynchronous AC motor having a wire-wound stator in operative relationship to said rotor which is connectable to an AC supply for generating when energized an electromagnetic motive force on the rotor to tend to drive it in the direction opposing movement of the shaft by the training person and thereby act as a braking force on the shaft independent of the movement thereof, the stator comprising a laminated metal sheet core which extends over part of the circular circumference of the rotor, partially surrounds the rotor, and has pole members facing the rotor; and wire winding provided on said pole members.

2. An energy absorbing unit as claimed in claim 1 wherein each pole member has a winding and wherein the windings of adjacent pole members are connected to different current circuits.

3. An energy absorbing unit as claimed in claim 2 for connection to a single phase AC supply wherein the windings on alternate pole members form the main phase and the auxiliary phase, respectively.

4. An energy absorbing unit as claimed in claim 1 further comprising a housing enclosing the asynchronous motor, which forms an elongated through air passage around the stator said passage being open at opposite ends thereof for the inlet and outlet of ventiliation air passing through the passage.

5. An energy absorbing unit as claimed in claim 1 further comprising a current regulator connected to the phase windings of the asynchronous motor.

6. An energy absorbing unit as claimed in claim 5 further comprising a control circuit in said current regulator and a signal source connected to the control circuit for supplying a control signal which is dependent of the size of a variable quantity in relation to a reference quantity.

7. An energy absorbing unit as claimed in claim 6 further comprising a signal transmitter for supplying a signal representing the rotational speed of the rotor, which is operatively connected to the rotor of the asynchronous machine.

8. An energy absorbing unit as claimed in claim 7 further comprising a multiplier and integrator circuit connected to the control circuit of the current regulator and to the signal transmitter for supplying a signal representing the work performed.

9. An energy absorbing unit as claimed in claim 8 further comprising a programming unit for supplying a programmed reference signal, which is connected to the multiplier and integrator circuit.

* * * * *

UNITED STATES PATENT OFFICE
CERTIFICATE OF CORRECTION

Patent No. 4,084,810   Dated April 18, 1978

Inventor(s) Lars Osten Forsman

It is certified that error appears in the above-identified patent and that said Letters Patent are hereby corrected as shown below:

Column 2, line 11, "asssembled" should be --assembled--
         line 18, "illstra-" should be --illustra- --
         line 65, "cape" should be --caps--
Column 3, line 8, after "associated" insert --planet--
Column 4, line 62, "ot" should be --not--
Column 5, line 30, "partically" should be --partially--
Column 6, line 24, "e" should be --be--
         line 28, after "effect" insert --being--
         line 66, "trough" should be --through--
         line 68, "controlld" should be --controlled--
Column 8, line 11, "ventiliation" should be --ventilation--
         line 26, "machine" should be --motor--

Signed and Sealed this

Seventh Day of November 1978

[SEAL]

Attest:

RUTH C. MASON
Attesting Officer

DONALD W. BANNER
Commissioner of Patents and Trademarks